United States Patent
Lacan et al.

(10) Patent No.: US 9,854,808 B2
(45) Date of Patent: Jan. 2, 2018

(54) COMPOSITION FOR STIMULATING PLANT VITALITY

(71) Applicant: Bionov, Avignon (FR)

(72) Inventors: Dominique Lacan, Montpellier (FR); Alain Dreyer, Chateauneuf de Gadagne (FR); Christian Yard, Combas (FR); Benoit Lemaire, Libourne (FR)

(73) Assignee: Bionov (FR)

( * ) Notice: Subject to any disclaimer, the term of this patent is extended or adjusted under 35 U.S.C. 154(b) by 51 days.

(21) Appl. No.: 14/653,066

(22) PCT Filed: Dec. 17, 2013

(86) PCT No.: PCT/EP2013/076950
§ 371 (c)(1),
(2) Date: Jun. 17, 2015

(87) PCT Pub. No.: WO2014/095900
PCT Pub. Date: Jun. 26, 2014

(65) Prior Publication Data
US 2015/0327558 A1   Nov. 19, 2015

(30) Foreign Application Priority Data
Dec. 17, 2012  (FR) ...................................... 12 62169

(51) Int. Cl.
| | | |
|---|---|---|
| *A01N 65/00* | (2009.01) | |
| *A61K 38/43* | (2006.01) | |
| *A61K 36/00* | (2006.01) | |
| *A01N 63/00* | (2006.01) | |
| *A01N 65/08* | (2009.01) | |
| *C05D 9/02* | (2006.01) | |
| *C05F 11/10* | (2006.01) | |

(52) U.S. Cl.
CPC .............. *A01N 63/00* (2013.01); *A01N 65/00* (2013.01); *A01N 65/08* (2013.01); *C05D 9/02* (2013.01); *C05F 11/10* (2013.01)

(58) Field of Classification Search
None
See application file for complete search history.

(56) References Cited

U.S. PATENT DOCUMENTS

| | | | |
|---|---|---|---|
| 5,616,323 A | 4/1997 | Ginoux et al. | |
| 6,084,152 A * | 7/2000 | Kwak | A01H 4/005 |
| | | | 435/252.2 |
| 6,984,630 B1 | 1/2006 | Descamps et al. | |

FOREIGN PATENT DOCUMENTS

| | | |
|---|---|---|
| CN | 1762922 A | 4/2006 |
| CN | 101406203 A | 4/2009 |
| CN | 101790952 A | 8/2010 |
| FR | 2716884 A1 | 9/1995 |
| FR | 2783523 A1 | 3/2000 |
| FR | 2785909 A1 | 5/2000 |
| GB | 2278347 A | 11/1994 |
| WO | 2004/095926 A2 | 11/2004 |
| WO | 2009042090 A2 | 4/2009 |
| WO | 2011/006543 A1 | 1/2011 |

OTHER PUBLICATIONS

Allen, R.D. Plant Physiol. 107: 1049-1054, 1995.
Alscher et al. (Plant Physiol., 100: 224-233, 2002).
Azvedo-Neto et al. Environ. Exp. Bot. 56: 87-94, 2006.
Ben Amor et al. J. Integr. Plant Biol. 49: 982-992, 2007.
Chamnongpol et al., Proc. Natl. Acad. Sci. USA. 12, 95(10): 5818-5823, 1998.
Dionisio-Sese, M.L.; Tobita, S. Plant Sci 135: 1-9, 1998.
Foyer et al. Plant Cell Environ. 17: 507-523, 1994.
Hernandez et al. Plant Cell and Environ. 23: 853-862, 2000.
Mansour et at. Gen. Applied Plant Physiol. 31: 29-41, 2005.
Raychaudhuri, S.S.; Deng, X.W. Botan. Rev. 66(1): 89-98, 2000.
Van Camp et al. Plant Physiol. 112: 1703-1714, 1996.
Yu, Q.; Rengel, Z. Annals of Botany 83: 175-182, 1999.

* cited by examiner

*Primary Examiner* — Alton Pryor
(74) *Attorney, Agent, or Firm* — Banner & Witcoff, Ltd.

(57) ABSTRACT

The present invention relates to the use of a composition comprising a superoxide dismutase (SOD) enzyme and/or an active plant extract containing SOD, for stimulating the overexpression of plant antioxidant enzymatic proteins, stimulating plant vitality and/or increasing plant productivity and/or preventively or curatively protecting said plants against biotic or abiotic stresses.

20 Claims, 1 Drawing Sheet

COMPOSITION FOR STIMULATING PLANT VITALITY

RELATED APPLICATION DATA

Figure 1:
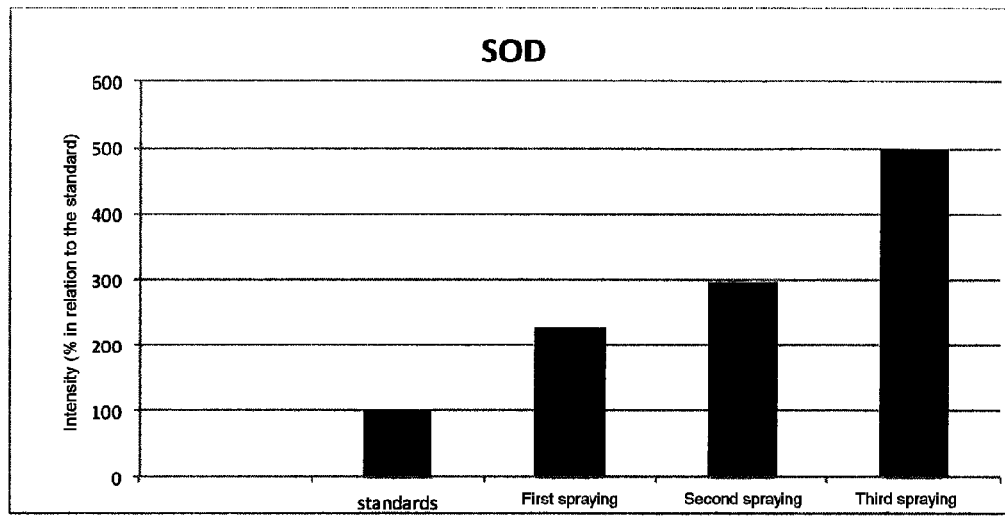

This application is a National Stage Application under 35 U.S.C. 371 of co-pending PCT application number PCT/EP2013/076950 designating the United States and filed Dec. 17, 2013; which claims the benefit of FR application number 1262169 and filed Dec. 17, 2012 each of which are hereby incorporated by reference in their entireties.

The present invention relates to the use of a composition comprising a superoxide dismutase (SOD) enzyme and/or an active plant extract containing SOD for stimulating overexpression of plant antioxidant enzyme proteins, stimulating plant vitality and/or protecting said plants against biotic or abiotic stresses.

Use of this composition according to the present invention improves the physiological and agronomic condition of plants by protecting them against biotic or abiotic stresses in particular. Furthermore, use of this composition according to the present invention should improve plant yield and quality.

Moreover, use of the composition according to the present invention is preventive and curative and may be carried out wet (by spraying or watering foliage) or dry (by adding to soil or cultivation substrate) on crops potentially subjected to various biotic or abiotic stresses.

The present invention, by placing the plant in improved conditions of defense against various attacks from its environment (parasitism, climatic attacks and the like), helps reduce the use of inputs, particularly phytopharmaceutical inputs, and thus provides better overall protection of the environment in ecologically-intensive agriculture conditions.

Oxygen is essential to cell functioning. However, it can be the source of toxic reactive oxygen forms that have a negative effect on plant development.

In biological systems, reactive oxygen species (ROS) represent free radicals, in particular such as the superoxide ($O_2^{\bullet-}$) radical, the hydroxyl ($OH^{\bullet}$) radical, nitric oxide ($NO^{\bullet}$) or lipid peroxide ($L\text{-}OO^{\bullet}$) radicals. These free radicals are atoms or molecules whose electron configuration is characterized by the presence of an unpaired valence electron. This feature makes these chemical species unstable and they may, in order to stabilize, quickly oxidize other biological molecules such as nucleic acids (DNA), enzyme proteins or membrane lipids, particularly polyunsaturated fatty acids (PFAs).

The superoxide ion is the free radical most commonly and most abundantly generated in cells. It thus represents a considerable danger to biological systems. Its toxicity depends mostly on its transformation into other more aggressive reagents, such as the hydroxyl ($OH^{\bullet}$) radical.

Plant cells carry on a permanent fight against ROS formation by means of various defense processes, particularly antioxidant actions, in order to detoxify themselves. These various plant defense processes are described below.

The first line of defense is provided by an enzyme called superoxide dismutase (SOD). There are three forms of SOD: one containing copper and zinc, namely Cu/Zn SOD; another containing manganese, Mn SOD; and finally a SOD containing iron, Fe SOD.

SOD plays a key role in protection against free radicals because it removes the superoxide ion. Superoxide dismutase is an enzyme able to induce dismutation of superoxide ions, according to the following two half-reactions:

$$O_2^{\bullet-} + SOD\text{-}M^{(n+1)+} \rightarrow O_2 + SOD\text{-}M^{n+}$$

$$O_2^{\bullet-} + 2H^+ + SOD\text{-}M^{n+} \rightarrow H_2O_2 + SOD\text{-}M^{(n+1)+},$$

with M representing the metal atom Fe (n=2), Cu (n=1) or Mn (n=2) of superoxide dismutase.

Nevertheless, as can be seen, this removal of the superoxide ion by SOD leads to the formation of hydrogen peroxide ($H_2O_2$), which is also toxic to the cell.

Therefore, the action of SOD must be supplemented by a second line of defense that eliminates $H_2O_2$.

This second line of defense is provided by two enzyme systems, that of catalase and that of the ascorbate/glutathione cycle of peroxidases, which ensure the destruction of $H_2O_2$.

Proteins that transport iron and copper (transferrin, ferritin) are also involved in cellular detoxification.

Small antioxidant molecules, such as glutathione, carotenoids, vitamin A, vitamin C (ascorbate), vitamin E (tocopherol), ubiquinone and flavonoids, are ROS or antioxidant traps (scavengers) stoichiometrically less powerful than enzymatic antioxidants. However, they help trap ROS, particularly secondary ROS, that may be formed.

Lastly, certain trace elements (copper, zinc, selenium) are essential to antioxidant enzyme activity.

Under normal biological conditions, plant cells produce ROS constantly, but in small amounts, particularly in photosynthesis systems, which are immediately neutralized by existing defense systems or which are used in certain cell signaling pathways.

An increase in free radical production and/or a lack of antioxidant substances leads to an oxidant/antioxidant ratio imbalance called oxidative stress.

Moreover, plants are continuously subjected to biotic stresses due to various parasitic attacks (fungi, viruses, bacteria, insects, etc.) or to abiotic stresses related to water deficit, mineral deficiencies, atmospheric pollution, presence of heavy metals, drought, cold, salt stress or aging. Each of these situations has a comparable impact on production yield and quality. Each of these situations may also induce an increase in ROS production, leading to a state of oxidative stress for the plant and its cells.

More precisely, by the expression "biotic stress" is meant, in the context of the present invention, stress resulting from the action of a living organism on another living plant organism, such as pathogen attack.

By the term "pathogen" is meant, in the context of the present invention, a biological agent responsible for an infectious disease in plants, particularly viruses, bacteria, parasites or prion-type proteins.

By the expression "abiotic stress" is meant, in the context of the present invention, stress related to an environmental change in a plant, particularly mineral deficiency, for example nitrogen deficiency, water deficit, atmospheric pollution, presence of heavy metals, cold, excessive salinity (salt stress) or aging.

By the expression "oxidative stress" is meant, in the context of the present invention, a type of attack on the components of a plant cell by reactive oxygen species (ROS), particularly free radicals such as the superoxide ($O2^{\bullet-}$) radical, the hydroxyl ($OH^{\bullet}$) radical, nitric oxide ($NO^{\bullet}$) or lipid peroxide ($L\text{-}OO^{\bullet}$) radicals. By extension, hydrogen peroxide ($H_2O_2$) is considered to be, according to the present invention, a ROS because, in the presence of iron in ionic form in plants, it dismutates to two hydroxyl radicals via the Haber-Weiss reaction.

Whatever the environmental conditions, the objective for mankind is to maintain crop productivity. Various strategies have been proposed to achieve this goal.

The use of various elicitors (glucans, chitin, oligogalacturonides, etc.) is often proposed to protect against pathogen attack by stimulating natural defense mechanisms (FR 2 783 523; WO 2011/006543).

Transgenic plants overexpressing proteins involved in pathogen defense have also been obtained (Chamnongpol et al., *Proc. Natl. Acad. Sci. USA*. 12, 95(10): 5818-5823, 1998), but use of this plant type remains problematic for farmers and consumers, partly due to the fact that environmental effects remain inadequately assessed.

Providing micronutrients such as zinc, copper, iron and manganese to protect against certain pathologies has been described in patent WO 2009/058857. A deficiency in certain micronutrients may lead to decreased growth in lupin as well as decreased SOD activity (Yu, Q.; Rengel, Z. *Annals of Botany* 83: 175-182, 1999). However, an excess of micronutrients can also be toxic to plants (Schubert T. S. *Plant Pathology Circular* 53, 1992).

Concerning abiotic stresses, international patent application WO 2004/095926 by Monsanto describes a method for treating plants with a mixture composed of an antioxidant and a pesticide. In this application, the Inventors explain that this treatment improves the resistance of plants and seeds to cold. However, this application applies only to improving the tolerance of plants to cold.

In the case of abiotic stress situations, antioxidant defenses, particularly SOD, are called upon. However, in order to protect against ROS overproduction, an increase in the enzymatic activity of antioxidant defenses, absent an increase in the synthesis (supply) of antioxidant proteins, is generally observed.

Consequently, these defense systems quickly become unable to cope with the large and continuous production of ROS. The response and adaptation by plants to these environmental conditions thus depend on the plants' ability to sufficiently produce antioxidant molecules, particularly SOD, in order to effectively fight the stress to which they are exposed (Raychaudhuri, S. S.; Deng, X. W. *Botan. Rev.* 66(1): 89-98, 2000).

For example, adaptation to saline soil by plants useful from an agronomic point of view is a major issue. However, salt stress causes an accumulation of ROS that can damage plant membrane lipids, proteins and DNA (Mansour et al. *Gen. Applied Plant Physiol.* 31: 29-41, 2005; Ben Amor et al. *J. Integr. Plant Biol.* 49: 982-992, 2007).

Alscher et al. (*Plant Physiol.*, 100: 224-233, 2002) have shown that neutralization of ROS by activation of antioxidant enzymes improves salt tolerance. A positive correlation between salt tolerance and increase in antioxidant enzyme activity has also been shown in peas (Hernandez et al. *Plant Cell and Environ.* 23: 853-862, 2000), *Arabidopsis* and rice (Qi et al. *J. Plant Physiol. Mol. Biol.* 30: 517-522, 2004; Dionisio-Sese, M. L.; Tobita, S. *Plant Sci* 135: 1-9, 1998), tomato, soy and corn (Azvedo-Neto et al. *Environ. Exp. Bot.* 56: 87-94, 2006).

Nevertheless, these antioxidant mechanisms are not sufficient to protect plants from high levels of stress. Indeed, as has been shown in situations of ozone stress, an increase in cellular antioxidant enzyme activity to fight ROS is observed first. The consequence is that the plant's supply of transcripts (mRNA) and antioxidant proteins is exhausted (Van Camp et al. *Plant Physiol.* 112: 1703-1714, 1996). A second observation follows therefrom, namely the inability of the plant's cells to maintain a sufficiently high level of antioxidant enzyme activity: the plant's defense systems are driven back and it can no longer fight.

The issue, therefore, is to maintain sufficiently high amounts of antioxidant proteins so that the plants can live under hostile or difficult environmental conditions.

The use of transgenic plants can respond to these problems. Indeed, the introduction of genes encoding SOD and ascorbate into tobacco seedlings enables these transgenic seedlings to improve their pesticide tolerance. However, the introduction of a single gene encoding an antioxidant enzyme leads to limited improvement in stress tolerance (Foyer et al. *Plant Cell Environ.* 17: 507-523, 1994; Allen, R. D. *Plant Physiol.* 107: 1049-1054, 1995). Furthermore, this type of approach leads to often complex genetic constructions that require the introduction of several antioxidant genes in order to obtain an effective improvement of resistance to stresses of various origins. Following the example of pathogen-resistant transgenic plants, use of this plant type is still problematic for farmers and consumers and the effects on the environment are, here again, inadequately assessed.

A common point with all these situations remains oxidative stress.

In order to respond to these problems, the aim of the present invention is, therefore, to induce, in a natural and sustainable manner, overexpression of antioxidant enzymes in the plant in order to improve the physiological and agronomic condition of the plant and, consequently, the productivity thereof, to effectively protect against plant aging, and to preventively or curatively protect against biotic or abiotic stresses.

The Inventors discovered, surprisingly, that the use of a superoxide dismutase (SOD)-based composition or an active plant extract comprising a superoxide dismutase (SOD) enzyme and/or an active plant extract containing SOD can stimulate overexpression of plant antioxidant enzyme proteins. These antioxidant enzyme proteins are, for example, SOD, catalase and ascorbate/glutathione peroxidases. Thus, the use according to the invention, that is, of a superoxide dismutase (SOD)-based composition or an active plant extract comprising a superoxide dismutase (SOD) enzyme and/or an active plant extract containing SOD, can also stimulate plant vitality and/or protect plants against biotic or abiotic stresses and/or increase plant productivity.

By "plant productivity" is meant in the context of the present invention the biomass formed during a given period of time (generally a day or a year) on a given surface area. Preferably, plant productivity reflects an increase in harvest weight in relation to an untreated control. It can also be referred to as yield. Productivity is thus expressed as a percentage.

The use according to the present invention can be carried out on plant seedlings, cuttings or adult plants, that is, at any stage of plant development. The use according to the present invention can also be carried out on seeds.

By "active plant extract containing superoxide dismutase" is meant, in the context of the present invention, any extract obtained from plants, advantageously from melon, having superoxide dismutase enzyme activity.

Advantageously, the SOD enzyme and/or the active plant extract according to the present invention are/is composed of or come/comes from a purified or unpurified protein extract of *Cucumis melo*.

More advantageously, the *Cucumis melo* is a descendant of cell line 95LS444 or one of the hybrid varieties arising from 95LS444.

In a particular embodiment, the present invention relates to the use of a superoxide dismutase (SOD)-based composition or an active plant extract comprising a superoxide dismutase (SOD) enzyme and/or an active plant extract containing SOD that can stimulate overexpression of plant antioxidant enzyme proteins, or stimulate plant vitality and/or protect plants against biotic or abiotic stresses and/or increase plant productivity, characterized in that the plant extract according to the present invention is a purified or unpurified protein extract of *Cucumis melo*, preferably a descendant of cell line 95LS444 or one of the hybrid varieties arising from 95LS444.

Preferably, the present invention relates to the use of a superoxide dismutase (SOD)-based composition or an active plant extract comprising a superoxide dismutase (SOD) enzyme and/or an active plant extract containing SOD that can stimulate overexpression of plant antioxidant enzyme proteins, or stimulate plant vitality and/or protect plants against biotic or abiotic stresses, characterized in that the plant extract according to the present invention is a purified or unpurified protein extract of *Cucumis melo*, preferably a descendant of cell line 95LS444 or one of the hybrid varieties arising from 95LS444.

Particularly, the use according to the present invention relates to a curative or preventive treatment for biotic or abiotic stress in plants.

In a particular embodiment of the present invention, the superoxide dismutase enzyme activity of the SOD and/or the active plant extract containing SOD is at least equal to 5 enzyme units per milligram, advantageously at least equal to 50 enzyme units per milligram of said extract.

In a preferred embodiment of the invention, the use of a composition comprising a superoxide dismutase (SOD) enzyme and/or an active plant extract containing SOD for stimulating overexpression of plant antioxidant enzyme proteins, stimulating plant vitality and/or protecting plants against biotic or abiotic stresses is characterized in that the SOD enzyme and/or the active plant extract are/is composed of or come/comes from a purified or unpurified protein extract of *Cucumis melo*, preferably a descendant of cell line 95LS444 or one of the hybrid varieties arising from 95LS444, having SOD enzyme activity equal to at least 5 enzyme units, advantageously at least equal to 50 enzyme units per milligram of said extract.

The active plant extract according to the invention may be obtained by methods well-known to the person skilled in the art, particularly by the method described in patent application FR 2 716 884.

Advantageously, the use of the composition according to the present invention aims at the stimulation of superoxide dismutase, peroxidase and catalase enzymes, preferentially superoxide dismutase and peroxidase enzymes.

Moreover, the composition according to the present invention contains at least one component selected from the group consisting of coenzyme Q10, vitamins such as vitamins $B_1$ to $B_{12}$, vitamins C, A and D or vitamin E, lipoic acid, glutathione, flavonoids and mineral elements such as potassium, magnesium, calcium or selenium, or mixtures thereof.

In a particular embodiment of the present invention, the SOD enzyme and/or the active plant extract are/is mixed with water, preferentially in the presence of at least one surfactant. Surfactants suited to the use according to the present invention are known to the person skilled in the art. The surfactant can be useful in improving contact between the plant and the active substances.

By the term "surfactant" is meant, in the context of the present invention, an amphiphilic compound that modifies the surface tension between two surfaces, thus making it possible to solubilize two immiscible phases. In the context of the present invention, this surfactant compound may be anionic, such as surfactants of type carboxylates ($R-CO_2^-$), surfactants of type sulfonates ($R-SO_3^-$) and surfactants of type sulfates ($SO_4^{2-}$); cationic, such as surfactants of type primary, secondary and tertiary ammoniums ($R_1-NH_3^+$, $R_2-NH_2^+$, $R_3-NH^+$) and quaternary ammoniums ($R_4-N^+$); zwitterionic, such as surfactants of type betaines or phospholipids; or nonionic, such as surfactants of type esters, polyols or alcohol ethoxylates.

In another particular embodiment of the present invention, the SOD enzyme content of the composition according to the invention is between 100 IU SOD/l and 10,000 IU SOD/l, preferentially between 100 IU SOD/l and 5000 IU SOD/l, even more preferentially equal to 1000 IU SOD/l.

According to a particular embodiment of the present invention, the SOD enzyme and/or the active plant extract are/is mixed with the soil and/or the compost and/or are/is added to the nutrient solution of the plants.

By "nutrient solution" is meant, in the context of the present invention, aqueous solution preferably comprising plant nutrient elements, such as, for example, trace elements, fertilizers, manures, plant protection agents, more preferably trace elements, fertilizers, manures.

According to another particular embodiment of the invention, the SOD enzyme and/or the active plant extract are/is sprayed on the plant to be treated.

According to another particular embodiment of the present invention, the SOD enzyme and/or the active plant extract are/is in powder form.

In addition, in another particular embodiment of the present invention, the SOD enzyme and/or the active plant extract are/is encapsulated.

According to the present invention, encapsulation can allow the vectorization and/or the sustained release of the active substances intended to treat plants. Generally, encapsulation can improve the efficacy of the use of the composition according to the present invention. Encapsulation may be carried out by techniques known to the person skilled in the art.

Furthermore, in another particular embodiment of the present invention, the composition used may contain one or more substance(s) selected from phytopharmaceutical agents, trace elements, nutrients or fertilizers, or any input used in plant cultivation, and mixtures thereof.

In a particular embodiment, the composition used is devoid of pesticide-type phytopharmaceutical or plant protection agents.

Moreover, another subject matter of the present invention relates to the use of the SOD enzyme and/or the active plant extract of the present invention, characterized in that the SOD enzyme and/or the active plant extract are/is obtained by:
 (1) crushing at least one plant that contains SOD,
 (2) optionally, drying the ground material and/or encapsulating the ground material,
 (3)a mixing the encapsulated or non-encapsulated ground material with water, optionally in the presence of a surfactant, or
 (3)b mixing the encapsulated or non-encapsulated ground material with soil and/or compost.

Advantageously, said plant is *Cucumis melo*, preferably a descendant of cell line 95LS444 or one of the hybrid varieties arising from 95LS444.

According to a particular embodiment of the present invention, the composition is sprayed on the plants to be treated or spread on the soil or the culture medium of the plants to be treated.

According to another particular embodiment of the present invention, the composition is used in powder form and mixed with soil or compost in order to then be provided to the plant.

Lastly, according to another particular embodiment of the present invention, the method of said invention is intended for use in curing or preventing biotic and/or abiotic stresses in plants.

By the term "plant" is meant, in the context of the present invention, field crop plants, industrial crop plants, forage plants, medicinal plants, vineyard plants, arboreal plants, marsh plants, horticultural plants, nursery plants, greenspace plants or ornamental plants, and mixtures thereof.

FIGURES

FIG. 1 shows a histogram evaluating the intensity of plant SOD production, expressed as a percentage, in relation to the standard. The measurement protocol is described in example 1. The standard represents 100%, then the results for plants having a first treatment one week after sowing (t=0), a second treatment one week later (t=1 week) and a third treatment two weeks after (t=3 weeks) are presented. The standard is an untreated plant.

Figure 2:
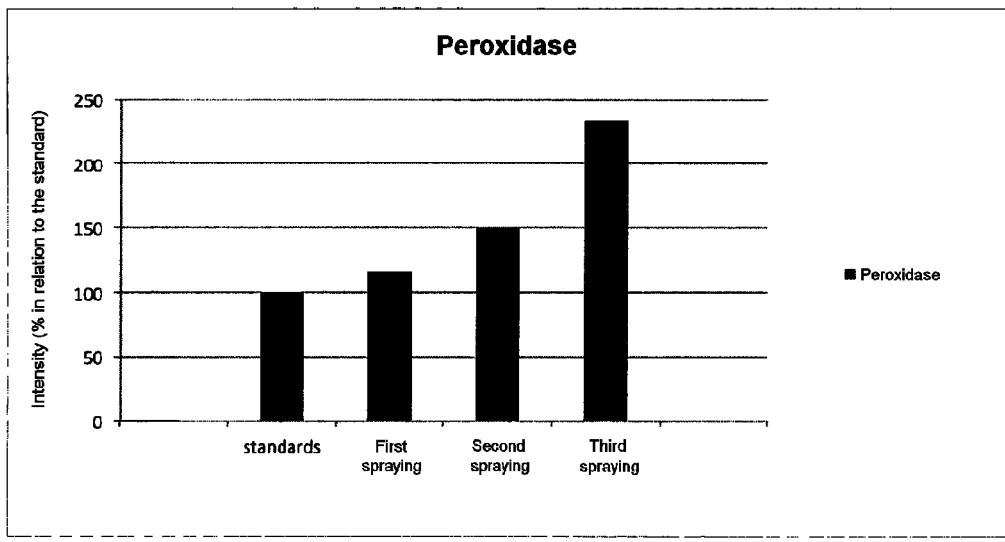

FIG. 2 represents a histogram evaluating the intensity of plant peroxidase production, expressed as a percentage, in relation to the standard. The measurement protocol is described in example 1. The standard represents 100%, then the results for plants having a first treatment one week after sowing (t=0), a second treatment one week later (t=1 week) and a third treatment two weeks after (t=3 weeks) are presented. The standard is an untreated plant.

The examples shown below serve to illustrate the present invention but in no case may be regarded as limiting the invention.

EXAMPLE 1: USE ON PLANTS NOT UNDER STRESS

The effectiveness of the melon extract in stimulating production of certain molecules involved in plant defenses, particularly superoxide dismutase (SOD) and peroxidases, and in increasing plant vitality was evaluated on various varieties of plants (lettuces, melon, tomato). Example 1 presents the results of one of these tests carried out on tomato plantlets.

Thus, between 0.001 g and 10 g, preferentially 0.01 g, of SOD-rich melon extract powder, the activity of which is 100 IU SOD/mg of powder, is mixed in a liter of water and this solution is sprayed on the plants.

Three preventive treatments with the melon extract solution will be applied: a first treatment one week after sowing (t=0), a second treatment one week later (t=1 week) and a third treatment two weeks after (t=3 weeks). The treated plants are compared with the untreated plants. At the conclusion of each treatment, 5 plants are sampled and the amount of SOD and peroxidase in the leaves is measured.

The evolution of SOD production (see FIG. 1) and of peroxidase production (see FIG. 2) in the tomato leaf is measured by immunoblotting (western blot).

The tomato leaves are ground in potassium phosphate buffer solution. The mixture obtained is then centrifuged and then filtered. The extracts thus obtained are then loaded on an electrophoresis gel in order to separate the various proteins. After separation, the proteins are transferred to nitrocellulose membranes. Antioxidant proteins (SODs and peroxidases) are detected by western blotting. Primary antibodies against tomato SODs and peroxidases are used to measure the expression of SODs and peroxidases. Next, a secondary antibody conjugated to alkaline phosphatase is used to reveal the primary antibodies. A scan of the membranes is used to measure the intensity of the bands obtained. The data are standardized by expressing the intensity of each band of interest for the treated plants in comparison with the corresponding band for the control plants.

The results presented in FIGS. 1 and 2 show that spraying the melon extract on the leaves of tomato plantlets induces endogenous synthesis of SOD and peroxidase. The synthesis of these two enzymes increases with number of sprayings.

EXAMPLE 2: USE ON PLANTS UNDER BIOTIC STRESS

As in example 1, the melon extract is sprayed on the plants and then the resistance of the plants to various parasites is tested.

As an example, significant results were obtained on a tomato/mildew (*Phytophtora infestans*) model, preventively and curatively.

The plants treated by spraying with the melon extract are compared with the untreated plants.

In the case of preventive treatments, the first results show that the treated plants are not attacked by the parasite, or are attacked very little. Efficacy is then correlated with number of treatments.

In the case of curative treatments, a reduction in symptoms of parasitic attack is observed a few days after the first treatment.

EXAMPLE 3: USE ON PLANTS UNDER ABIOTIC STRESS

As in example 1, the melon extract is sprayed on the plants and then the resistance of the plants to various stresses (water stress, cold, drought, ozone, micronutrient deficiency, etc.) is tested.

As an example, significant results were obtained on a model of water stress on tomato.

Plants treated with melon extract are compared with untreated plants.

In the case of preventive treatments, the treated plants are not affected by water stress, or are affected very little. Efficacy is then correlated with number of treatments.

In the case of curative treatments, a reduction in symptoms related to water stress is observed a few days after the first treatment.

The invention claimed is:

1. A method of stimulating overexpression of antioxidant enzyme proteins in plants comprising applying a composition to plants, wherein the composition is spread on a soil or a culture medium of the plants or wherein the composition is mixed with the soil or the compost or is added to the nutrient solution of the plants, and wherein the composition comprises a superoxide dismutase (SOD) enzyme and/or an active plant extract containing SOD, said SOD or said active plant extract being composed of or coming from a purified or unpurified protein extract of *Cucumis melo*.

2. The method of claim 1, wherein said composition stimulates plant vitality and/or increases plant productivity and/or preventively or curatively protects plants against biotic or abiotic stresses.

3. The method of claim 1, wherein the *Cucumis melo* is a descendant of cell line 95LS444 or one of hybrid varieties arising from 95LS444.

4. The method of claim 1, wherein the SOD enzyme and/or the active plant extract containing SOD have/has SOD enzyme activity equal to at least 5 enzyme units per milligram of said extract.

5. The method of claim 1, wherein the antioxidant enzyme proteins are superoxide dismutases, peroxidases and catalases.

6. The method of claim 1, wherein the composition contains at least one component selected from the group consisting of coenzyme Q10, vitamins such as vitamins $B_1$ to $B_{12}$, vitamins C, A and D or vitamin E, lipoic acid, glutathione, flavonoids and mineral elements, or mixtures thereof.

7. The method of claim 1, wherein the SOD enzyme and/or the active plant extract are/is mixed with water.

8. The method of claim 1, wherein the SOD enzyme and/or active plant extract content of the composition is between 100 IU SOD/l and 10,000 IU SOD/l.

9. The method of claim 1, wherein the composition is sprayed on the plants.

10. The method of claim 1, wherein the SOD enzyme or the active plant extract is mixed with the soil or the compost or is added to the nutrient solution of the plants.

11. The method of claim 1, wherein the SOD enzyme and/or the active plant extract are/is in powder form.

12. The method of claim 1, wherein the SOD enzyme and/or the active plant extract are/is encapsulated.

13. The method of claim 1, wherein the composition contains one or more substance(s) selected from phytopharmaceutical agents, trace elements, nutrients or fertilizers, or any input used in plant cultivation, and mixtures thereof.

14. The method of claim 1, wherein the SOD enzyme and/or the active plant extract are/is obtained by:
  (1) crushing at least one plant that contains SOD,
  (2) optionally, drying the ground material and/or encapsulating the ground material,
  (3)a mixing the encapsulated or non-encapsulated ground material with water, optionally in the presence of a surfactant, or
  (3)b mixing the encapsulated or non-encapsulated ground material with soil and/or compost.

15. The method of claim 5, wherein the antioxidant enzyme proteins are superoxide dismutases and peroxidases.

16. The method of claim 6, wherein the mineral elements is potassium, magnesium, calcium or selenium.

17. The method of claim 7, wherein the SOD enzyme and/or the active plant extract are/is mixed with water in the presence of at least one surfactant.

18. The method of claim 8, wherein the SOD enzyme and/or active plant extract content of the composition is between 100 IU SOD/l and 5000 IU SOD/l.

19. The method of claim 8, wherein the SOD enzyme and/or active plant extract content of the composition is equal to 1000 IU SOD/l.

20. The method of claim 1, wherein the SOD enzyme and/or the active plant extract containing the SOD have/has SOD enzyme activity at least equal to 50 enzyme units per milligram of said extract.

* * * * *